United States Patent
Mutel et al.

(10) Patent No.: US 7,138,404 B2
(45) Date of Patent: Nov. 21, 2006

(54) 4-AMINOPYRIMIDINE DERIVATIVES

(75) Inventors: Vincent Mutel, Brunstatt (FR); Jens-Uwe Peters, Grenzach-Wyhlen (DE); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 480 days.

(21) Appl. No.: 10/135,150

(22) Filed: Apr. 29, 2002

(65) Prior Publication Data

US 2003/0022907 A1  Jan. 30, 2003

(30) Foreign Application Priority Data

May 23, 2001  (EP) ................... 01112564

(51) Int. Cl.
*A61K 31/513* (2006.01)
*C07D 43/02* (2006.01)

(52) U.S. Cl. ................ 514/269; 544/317
(58) Field of Classification Search .......... 514/269; 544/317
See application file for complete search history.

(56) References Cited

U.S. PATENT DOCUMENTS

| | | | | |
|---|---|---|---|---|
| 3,896,129 | A | * 7/1975 | Santilli et al. | 544/295 |
| 3,901,887 | A | * 8/1975 | Santilli et al. | 544/317 |
| 3,910,910 | A | * 10/1975 | Santilli et al. | 544/314 |
| 3,940,394 | A | * 2/1976 | Santilli et al. | 544/317 |
| 4,423,047 | A | * 12/1983 | Benneche et al. | 514/274 |
| 4,447,609 | A | 5/1984 | Peeters | 544/317 |
| 4,933,348 | A | * 6/1990 | Mase et al. | 514/274 |
| 5,262,385 | A | * 11/1993 | Goh et al. | 504/239 |
| 5,270,289 | A | * 12/1993 | Harde et al. | 504/243 |
| 5,684,011 | A | * 11/1997 | Fitzjohn et al. | 514/274 |
| 5,981,537 | A | * 11/1999 | Nugent et al. | 514/274 |
| 6,043,248 | A | * 3/2000 | Nugent et al. | 514/256 |
| 6,124,306 | A | * 9/2000 | Morris et al. | 514/274 |
| 6,410,729 | B1 | * 6/2002 | Spohr et al. | 544/320 |
| 6,420,385 | B1 | * 7/2002 | Spohr et al. | 514/310 |
| 6,727,251 | B1 | * 4/2004 | Bebbington et al. | 514/241 |
| 2004/0176385 | A1 | * 9/2004 | Nuss et al. | 514/252.14 |

FOREIGN PATENT DOCUMENTS

| | | | |
|---|---|---|---|
| EP | 061 019 | | 9/1982 |
| EP | 061019 | * | 9/1982 |
| EP | 0 191443 | | 8/1986 |
| EP | 191443 | * | 8/1986 |
| FR | 1013704 | | 8/1952 |

OTHER PUBLICATIONS

Schlaeger et al., *Cytotechnology*, 30, pp. 71-83 (1999).

* cited by examiner

*Primary Examiner*—James O. Wilson
*Assistant Examiner*—Tamthom N. Truong
(74) *Attorney, Agent, or Firm*—George W. Johnston; Patricia S. Rocha-Tramaloni; Kimberly J. Prior

(57) ABSTRACT

This invention is 4-aminopyrimidine derivatives of the formula

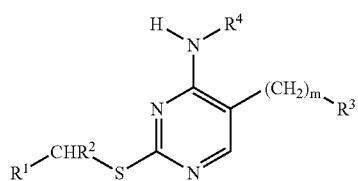

wherein $R^1$, $R^2$, $R^3$ and $R^4$ are as defined in the specification or a pharmaceutically acceptable salt thereof. The invention also is the preparation of compounds of formula I, pharmaceutical compositions containing therapeutically effective amounts of compounds of formula I or pharmaceutically acceptable salts thereof and to a method of treatment comprising administering therapeutically effective amounts of the compound of formula I for the prevention or treatment of mGluR5 receptor mediated disorders.

24 Claims, No Drawings

4-AMINOPYRIMIDINE DERIVATIVES

FIELD OF INVENTION

The present invention relates to 4-aminopyrimidine derivatives of the formula

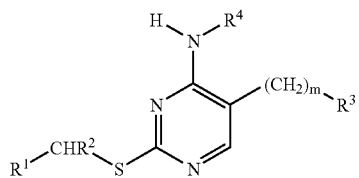

Compounds of formula I are metabotropic glutamate (mGluR 5a) receptor antagonists and are useful in the treatment of disorders responsive to mediation of the mGluR 5 a receptors.

BACKGROUND

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and GluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated fully or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression and pain.

Selective mGluR5 antagonists are especially useful for the treatment of anxiety and pain.

SUMMARY

The present invention is a compound of formula

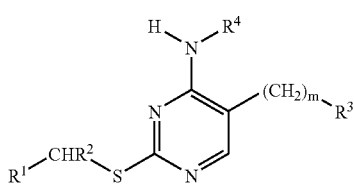

or a pharmaceutically acceptable salt thereof, wherein
$R^1$ is selected from the group consisting of
$C_2$–$C_6$-alkenyl,
$C_2$–$C_6$-alkinyl,
$C_3$–$C_6$-cycloalkyl,
—C(O)O—($C_1$–$C_6$)-alkyl,
—C(O)O—($C_2$–$C_6$)-alkenyl,
—C(O)O—($C_2$–$C_6$)-alkinyl,
—C(O)O—($C_3$–$C_6$)-cycloalkyl,
—C(O)O—$CH_2$-($C_3$–$C_6$)-cycloalkyl,
—C(O)O—($C_3$–$C_6$)-cycloalkyl substituted by at least one $C_1$–$C_6$-alkyl,
—C(O)O—$CH_2$—($C_3$–$C_6$)-cycloalkyl, substituted by at least one $C_1$–$C_6$-alkyl,
—C(O)O—$CH_2$-heteroaryl,
—C(O)O—$CH_2$-heteroaryl substituted by at least one substituent selected from the group $C_1$–$C_6$-alkyl, unsubstituted heteroaryl and heteroaryl substituted by at least one substituent selected from the group consisting of $C_1$–$C_6$-alkyl, $C_2$–$C_6$-alkenyl, $C_2$–$C_6$-alkinyl, $C_3$–$C_6$-cycloalkyl and halogen;
$R^2$ is hydrogen or $C_1$–$C_6$-alkyl;
$R^3$ is selected from the group consisting of
unsubstituted aryl, aryl substituted by at least one substituent selected from the group consisting of $C_1$–$C_6$-alkyl, $C_2$–$C_6$-alkenyl, $C_2$–$C_6$-alkinyl, $C_3$–$C_6$-cycloalkyl, halogen, and cyano, unsubstituted heteroaryl and heteroaryl substituted by at least one substituent selected from the group consisting of $C_1$–$C_6$-alkyl, $C_2$–$C_6$-alkenyl, $C_2$–$C_6$-alkinyl, $C_3$–$C_6$-cycloalkyl, halogen, cyano, and —C(O)O—($C_1$–$C_6$)-alkyl;
$R^4$ is hydrogen or $C_1$–$C_6$-alkyl; and
m is 0, 1 or 2.

It has now surprisingly been found that the compounds of formula I are metabotropic glutamate receptor antagonists. Compounds of formula I are distinguished by having valuable therapeutic properties. They can be used in the treatment or prevention of mGluR5 receptor mediated disorders.

One object of the present invention is compounds of formula I and pharmaceutically acceptable salts thereof. A further object is the preparation of the compounds of formula I and pharamceutically acceptable salts thereof. Pharmaceutical compositions containing a therapeutically effective amount of a compound of formula I or a pharmaceutically acceptable salts thereof, and their manufacture are also an object of the present invention. Another object of the present invention is a method of treatment, control or prevention of mGluR5 receptor mediated disorders, comprising administering a therapeutically effective amount of a compound of formula I, or a pharmaceutically acceptable salt thereof to a person in need of such treatment. The most preferred indication in accordance with the method of treatment of the present invention is the treatment or alleviation of anxiety and pain.

DETAILED DESCRIPTION

The following definitions of general terms used in the present description apply irrespective of whether the terms in question appear alone or in combination.

The term "($C_1$–$C_6$)-alkyl" ("lower alkyl") used in the present description denotes straight-chain or branched saturated hydrocarbon residues with 1 to 6 carbon atoms, preferably with 1 to 4 carbon atoms, such as methyl, ethyl, n-propyl, i-propyl, n-butyl, t-butyl and the like.

The terms "$C_2$–$C_6$-alkenyl" or "$C_2$–$C_6$-alkinyl" denote straight-chain or branched unsaturated hydrocarbon residues with 2 to 6 carbon atoms, preferably with 2 to 4 carbon atoms, such as ethenyl, ethinyl, 1-propenyl, 2-propenyl, propargyl, 1-butenyl and the like.

The terms "unsubstituted" and "substituted" are used in the same context as generally used in organic chemistry.

The term "$C_3$–$C_6$-cycloalkyl" means a cycloalkyl group containing 3 to 6 carbon atoms, such as cyclopropyl, cyclobutyl, cyclopentyl or cyclohexyl.

The term "halogen" denotes fluorine, chlorine, bromine and iodine.

"Aryl" represents an aromatic carbocyclic group consisting of one individual ring, or one or more fused rings in which at least one ring is aromatic in nature. Preferred aryl groups are phenyl or naphthyl.

The term "heteroaryl" refers to an aromatic 5- or 6-membered ring containing one or more heteroatoms selected from nitrogen, oxygen or sulphur, or to a fused-ring aromatic group comprising two 5- or 6-membered rings, in which one or both rings can contain one or more heteroatoms selected from nitrogen, oxygen or sulphur. Examples of such heteroaryl groups are furyl, pyrrolyl, thienyl (thiophenyl), 1H-imidazolyl, 2H-imidazolyl, 4H-imidazolyl, 1H-pyrazolyl, 3H-pyrazolyl, 4H-pyrazolyl, 1,2-oxazolyl, 1,3-oxazolyl, [1,2,4]triazolyl, [1,2,3]triazolyl, [1,2,4]oxadiazolyl, [1,3,4]oxadiazolyl, [1,2,3]oxadiazolyl, tetrazolyl, [1,2,3,4] oxatriazolyl, [1,2,3,5]oxatriazolyl, 1,3-thiazolyl, 1,2-thiazolyl, pentazolyl, pyridyl, pyrazinyl, pyrimidinyl, pyridazinyl, benzofuryl (benzofuranyl), benzothienyl (benzothiophenyl), benzimidazolyl, benzo [1,4]dioxinyl, benzoxazolyl, benzothiazolyl, indolyl, isoindolyl, quinolyl, isoquinolyl and the dihydro derivatives of said 5- or 6-membered heteroaromatic rings.

Preferred heteroaryl groups are furyl, pyrrolyl and thienyl as well as [1,2,4]oxadiazolyl or isoxazolyl.

The term "pharmaceutically acceptable salt" refers to any salt derived from a pharmaceutically acceptable inorganic or organic acid or base.

Preferred compounds of formula I are those in which m is 0 or 1. Especially preferred are those compounds in which m is 1.

More preferred are compounds of formula I in which m is 1 and $R^3$ is selected from the group consisting of unsubstituted heteroaryl and heteroaryl substituted by at least one substituent selected from the group consisting of $C_1$–$C_6$-alkyl, $C_2$–$C_6$-alkenyl, $C_2$–$C_6$-alkinyl, $C_3$–$C_6$-cycloalkyl, halogen or cyano.

The following are more preferred compounds of formula I in which m is 1, $R^3$ signifies unsubstituted heteroaryl or heteroaryl substituted by at least one $C_1$–$C_6$-alkyl, $C_2$–$C_6$-alkenyl, $C_2$–$C_6$-alkinyl, $C_3$–$C_6$-cycloalkyl, halogen or cyano, and $R^1$ is —C(O)O—($C_1$–$C_6$)-alkyl, —C(O)O—($C_2$–$C_6$)-alkenyl, —C(O)O—($C_2$–$C_6$)-alkinyl, —C(O)O—($C_3$–$C_6$)-cycloalkyl, —C(O)O—$CH_2$—($C_3$–$C_6$)-cycloalkyl, —C(O)O—($C_3$–$C_6$)-cycloalkyl, or —C(O)—$CH_2$—($C_3$–$C_6$)-cycloalkyl wherein the cycloalkyl ring is substituted by at least one $C_1$–$C_6$-alkyl, —C(O)O—$CH_2$-heteroaryl or —C(O)O—$CH_2$-heteroaryl substituted by at least one $C_1$–$C_6$-alkyl. The compounds are selected from the group consisting of (4-amino-5-thiophen-2-ylmethyl-pyrimidin-2-ylsulfanyl)-acetic acid methyl ester, (4-amino-5-thiophen-2-ylmethyl-pyrimidin-2-ylsulfanyl)-acetic acid ethyl ester, [4-amino-5-(1-methyl-1H-pyrrol-2-ylmethyl)-pyrimidin-2-ylsulfanyl]-acetic acid ethyl ester, 2-(4-amino-5-thiophen-2-ylmethyl-pyrimidin-2-ylsulfanyl)-propionic acid methyl ester, (4-amino-5-thiophen-3-ylmethyl-pyrimidin-2-ylsulfanyl)-acetic acid ethyl ester, (4-amino-5-furan-3-ylmethyl-pyrimidin-2-ylsulfanyl)-acetic acid ethyl ester, [4-amino-5-(3-methyl-thiophen-2-ylmethyl)-pyrimidin-2-ylsulfanyl]-acetic acid ethyl ester, [4-amino-5-(5-chloro-thiophen-2-ylmethyl)-pyrimidin-2-ylsulfanyl]-acetic acid ethyl ester, [4-amino-5-(5-ethyl-furan-2-ylmethyl)-pyrimidin-2-ylsulfanyl]-acetic acid ethyl ester, [4-amino-5-(5-methyl-furan-2-ylmethyl)-pyrimidin-2-ylsulfanyl]-acetic acid ethyl ester, (4-ethylamino-5-thiophen-2-ylmethyl-pyrimidin-2-ylsulfanyl)-acetic acid ethyl ester, and (4-isobutylamino-5-thiophen-2-ylmethyl-pyrimidin-2-ylsulfanyl)-acetic acid ethyl ester.

Further preferred are those compounds of formula I in which m is 1, $R^3$ signifies unsubstituted heteroaryl or heteroaryl substituted by one or more $C_1$–$C_6$-alkyl, $C_2$–$C_6$-alkenyl, $C_2$–$C_6$-alkinyl, $C_3$–$C_6$-cycloalkyl, halogen or cyano, and $R^1$ signifies unsubstituted heteroaryl or heteroaryl substituted by one or more $C_1$–$C_6$-alkyl, $C_2$–$C_6$-alkenyl, $C_2$–$C_6$-alkinyl, $C_3$–$C_6$-cycloalkyl or halogen. An example of such a compound is 2-([1,2,4]Oxadiazol-3-ylmethylsulfanyl)-5-thiophen-2-ylmethyl-pyrimidin-4-ylamine.

Especially preferred also are compounds of formula 1 in which m is 1, $R^3$ signifies unsubstituted heteroaryl or heteroaryl substituted by one or more $C_1$–$C_6$-alkyl, $C_2$–$C_6$-alkenyl, $C_2$–$C_6$-alkinyl, $C_3$–$C_6$-cycloalkyl, halogen or cyano, and $R^1$ signifies $C_2$–$C_6$-alkenyl, $C_2$–$C_6$-alkinyl or $C_3$–$C_6$-cycloalkyl. Examples of these compounds are selected from the group consisting of
2-prop-2-ynylsulfanyl-5-thiophen-2-ylmethyl-pyrimidin-4-ylamine,
2-allylsulfanyl-5-thiophen-2-ylmethyl-pyrimidin-4-ylamine, and
2-cyclopropylmethylsulfanyl-5-thiophen-2-ylmethyl-pyrimidin-4-ylamine.

Also preferred are compounds of formula I in which m is 1 and $R^3$ is unsubstituted aryl or aryl substituted by at least one substituent selected from the group consisting of $C_1$–$C_6$-alkyl, $C_2$–$C_6$-alkenyl, $C_2$–$C_6$-alkinyl, $C_3$–$C_6$-cycloalkyl, halogen and cyano.

Especially preferred are compounds of formula I in which m is 1, $R^3$ is selected from the group consisting of unsubstituted aryl and aryl substituted by at least one substituent selected from the group consisting of $C_1$–$C_6$-alkyl, $C_2$–$C_6$-alkenyl, $C_2$–$C_6$-alkinyl, $C_3$–$C_6$-cycloalkyl, halogen and cyano, and $R^1$ is —C(O)O—($C_1$–$C_6$)-alkyl, —C(O)O—($C_2$–$C_6$)-alkenyl, —C(O)O—($C_2$–$C_6$)-alkinyl, —C(O)O—($C_3$–$C_6$)-cycloalkyl, —C(O)O—$CH_2$—($C_3$–$C_6$)-cycloalkyl, C(O)O—(C$_3$–C$_6$)-cycloalkyl or —C(O)O—CH$_2$—(C$_3$–C$_6$)-cycloalkyl substituted by at least one substituent selected from the group consisting of C$_1$–C$_6$-alkyl, —C(O)O—CH$_2$-heteroaryl and C(O)O—CH$_2$-heteroaryl substituted by at least one C$_1$–C$_6$-alkyl. The following are examples of such compounds selected from the group consisting of (4-amino-5-benzyl-pyrimidin-2-ylsulfanyl)-acetic acid ethyl ester, [4-amino-5-(4-bromo-benzyl)-pyrimidin-2-ylsulfanyl]-acetic acid ethyl ester, (4-amino-5-benzyl-pyrimidin-2-ylsulfanyl)-acetic acid allyl ester, (4-amino-5-benzyl-pyrimidin-2-ylsulfanyl)-acetic acid prop-2-ynyl ester, (4-amino-5-benzyl-pyrimidin-2-ylsulfanyl)-acetic acid 2-methyl-cyclopropylmethyl ester, (4-amino-5-benzyl-pyrimidin-2-ylsulfanyl)-acetic acid cyclobutylmethyl ester, (4-amino-5-benzyl-pyrimidin-2-ylsulfanyl)-acetic acid cyclobutyl ester, (4-amino-5-benzyl-pyrimidin-2-ylsulfanyl)-acetic acid cyclopentyl ester, (4-amino-5-benzyl-pyrimidin-2-ylsulfanyl)-acetic acid 5-methyl-isoxazol-3-ylmethyl ester, (4-amino-5-benzyl-pyrimidin-2-ylsulfanyl)-acetic acid cyclopropylmethyl ester, and (4-amino-5-benzyl-pyrimidin-2-yloxy)-acetic acid methyl ester.

Additional preferred compounds of formula I are those in which m is 1, R$^3$ is unsubstituted aryl or aryl substituted by at least one substituent selected from the group consisting of C$_1$–C$_6$-alkyl, C$_2$–C$_6$-alkenyl, C$_2$–C$_6$-alkinyl, C$_3$–C$_6$-cycloalkyl, halogen and cyano: and R$^1$ is unsubstituted heteroaryl or heteroaryl substituted by at least one substituent selected from the group consisting of C$_1$–C$_6$-alkyl, C$_2$–C$_6$-alkenyl, C$_2$–C$_6$-alkinyl, C$_3$–C$_6$-cycloalkyl and halogen. Exemplary of this class of preferred compound is 5-Benzyl-2-(3-cyclopropyl-[1,2,4]oxadiazol-5-ylmethylsulfanyl)-pyrimidin-4-ylamine.

Further preferred compounds of formula I are those in which m is 1, R$^3$ is unsubstituted aryl or aryl substituted by at least one substituent selected from the group consisting of C$_1$–C$_6$-alkyl, C$_2$–C$_6$-alkenyl, C$_2$–C$_6$-alkinyl, C$_3$–C$_6$-cycloalkyl, halogen and cyano; and R$^1$ is selected from the group consisting of C$_2$–C$_6$-alkenyl, C$_2$–C$_6$-alkinyl and C$_3$–C$_6$-cycloalkyl. Exemplary of such a compound is 4-(2-Allylsulfanyl-4-amino-pyrimidin-5-ylmethyl)-benzonitrile.

Also preferred are compounds of formula I in which m is 1 and R$^3$ signifies C$_3$–C$_6$-cycloalkyl. An example of such a compound is (4-amino-5-cyclopropylmethyl-pyrimidin-2-yl-sulfanyl)-acetic acid ethyl ester.

Further preferred compounds of formula I are those in which m is 0. Especially preferred are those, in which m is 0 and R$^1$ is selected from the group consisting of —C(O)O—(C$_1$–C$_6$)-alkyl, —C(O)O—(C$_2$–C$_6$)-alkenyl, —C(O)O—(C$_2$–C$_6$)-alkinyl, —C(O)O—(C$_3$–C$_6$)-cycloalkyl, —C(O)O—CH$_2$—(C$_3$–C$_6$)-cycloalkyl, —C(O)O—(C$_3$–C$_6$)-cycloalkyl or —C(O)O—CH$_2$—(C$_3$–C$_6$)-cycloalkyl substituted by at least one C$_1$–C$_6$-alkyl, —C(O)O—CH$_2$-heteroaryl and —C(O)O—CH$_2$-heteroaryl substituted by at least one C$_1$–C$_6$-alkyl. The following compounds selected from the group consisting of [4-amino-5-(2,4-dichloro-phenyl)-pyrimidin-2-ylsulfanyl]-acetic acid ethyl ester, 4-amino-2-ethoxycarbonylmethylsulfanyl-pyrimidine-5-carboxylic acid ethyl ester, and [4-amino-5-(2-chloro-phenyl)-pyrimidin-2-ylsulfanyl]-acetic acid ethyl ester are exemplary of such compounds.

Preferred compounds of formula I are those in which R$^2$ is hydrogen.

Also preferred are compounds of formula I, wherein R$^4$ signifies hydrogen.

Preferred compounds of formula I are also those wherein R$^3$ signifies a heteroaryl group selected from unsubstituted furyl, pyrrolyl and thienyl and furyl, pyrrolyl and thienyl substituted by substituted by at least one substituent selected from C$_1$–C$_6$-alkyl, C$_2$–C$_6$-alkenyl, C$_2$–C$_6$-alkinyl, C$_3$–C$_6$-cycloalkyl, halogen and cyano.

Also preferred are compounds of formula I wherein R$^1$ signifies [1,2,4]oxadiazolyl optionally substituted by at least one substituent selected from the group consisting of C$_1$–C$_6$-alkyl, C$_2$–C$_6$-alkenyl, C$_2$–C$_6$-alkinyl, C$_3$–C$_6$-cycloalkyl or halogen.

The compounds of formula I and their pharmaceutically acceptable salts can be manufactured by reacting a compound of formula

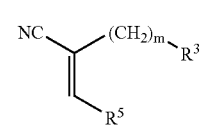

II wherein R$^5$ signifies phenylamino, 3-thienylamino or morpholino, and R$^3$ and m have the significances as defined before, with thiourea to obtain a compound of formula

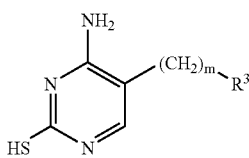

III and reacting this compound with a compound of formula

IV wherein R$^1$ and R$^2$ have the significances as defined before and X is halogen, and, if desired, converting the amino group into an aminoalkyl group, thereby forming a compound of formula

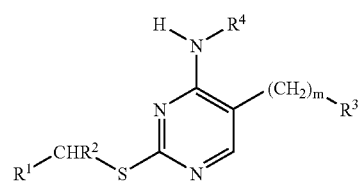

I wherein R$^4$ is hydrogen or C$_1$–C$_6$-alkyl, and, if desired, converting a compound of formula I into a pharmaceutically acceptable salt.

In accordance with the invention, a 4-aminopyrimidine derivative of formula III is formed by condensation of thiourea (1.1 eq.) with an appropriately substituted compound of formula II. Compounds of formula III, wherein m signifies 1 or 2, are prepared from thiourea and a 2-substituted 3-phenylamino-acrylonitrile. The condensation reaction is carried out in ethanol under reflux using a catalytic amount of a strong base like sodium ethoxide (e.g. 0.1 eq). The product can be obtained as precipitate after reducing the solvent and cooling (Scheme 1).

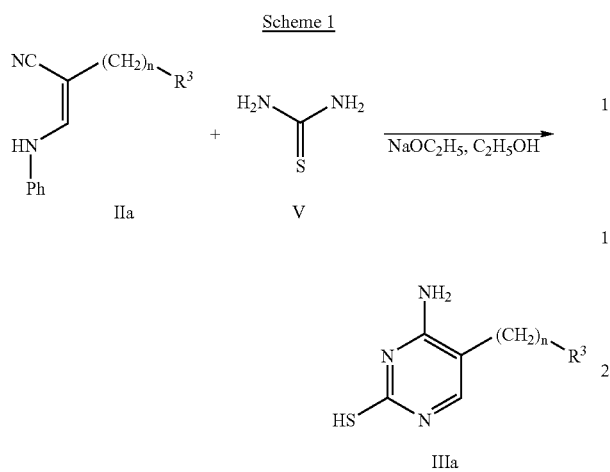

The 2-substituted 3-phenylamino-acrylonitrile of formula IIa, wherein n is 1 or 2, is prepared by condensation of an aldehyde of formula VII, wherein p is 0 or 1, with β-anilinopropionitrile (VI) (scheme 2). Treatment of a solution of VII and VI in dimethylsulfoxide with strong base like potassium-tert-butylate (1 eq.) gives the condensation product IIa.

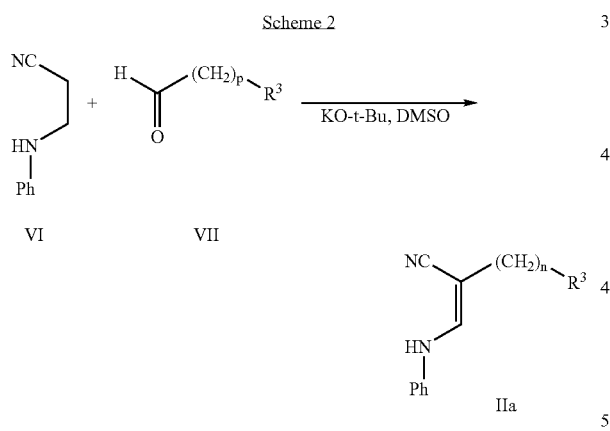

4-Aminopyrimidines of formula III, wherein m signifies 0, are obtained by the procedures described in schemes 3 and 4.

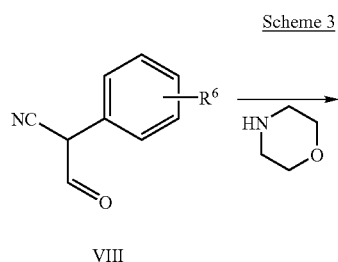

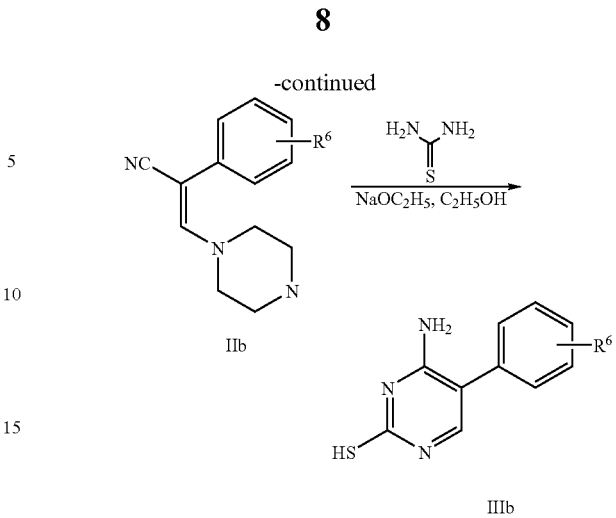

For example, compounds of formula IIIb are prepared by reacting a 2-formyl-2-phenylacetonitrile of formula VIII with morpholine followed by condensation of the obtained 3-morpholino-2-phenylacrylonitrile of formula IIb with thiourea (scheme 3).

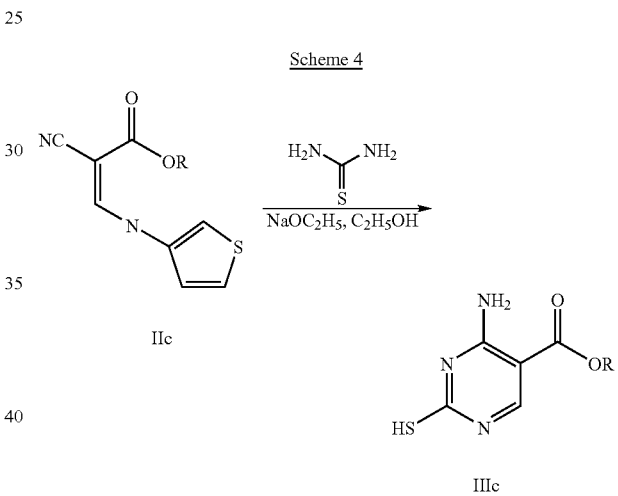

A 4-amino-2-sulfanyl-pyrimidine-5-carboxylic acid ester of formula IIIc is obtained by condensation of a 2-cyano-3-(3-thienylamino)-2-propenoic acid ester of formula IIc with thiourea (scheme 4).

The reaction of the 5-substituted 4-amino-pyrimidine-2-thiols of formula III with appropiate alkyl halides of formula IV leads to the corresponding 5-substituted 2-alkylsulfanyl-pyrimidin-4-ylamines of formula Ia. The reaction is carried out at room temperature in a IM solution of sodium methoxide in methanol or of sodium ethoxide in ethanol (scheme 5).

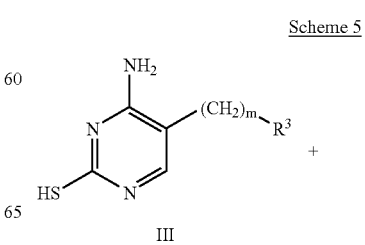

-continued

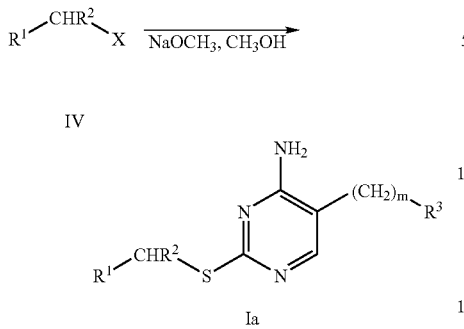

Compounds of formula I, wherein R¹ is alkoxycarbonyl and R² is hydrogen, are prepared by either directly reacting a compound of formula III with an alkyl bromoacetate or by the procedure as described in scheme 6.

A 5-substituted (4-amino-pyrimidin-2-ylsulfanyl)-acetic acid of formula Ib is obtained by reacting a compound of formula III with 2-chloro-acetic acid IX. Esterification of Ib with dicyclohexylcarbodiimide (DCC) and the appropiate alcohol $R^7OH$, in which $R^7$ is $(C_1-C_6)$-alkyl, $(C_2-C_6)$-alkenyl, $(C_2-C_6)$-alkinyl, $(C_3-C_6)$-cycloalkyl, —$CH_2$—$(C_3-C_6)$-cycloalkyl or —$CH_2$-heteroaryl wherein the heteroaryl ring maybe substituted by one or more $(C_1-C_6)$-alkyl, leads to the ester of formula Ic.

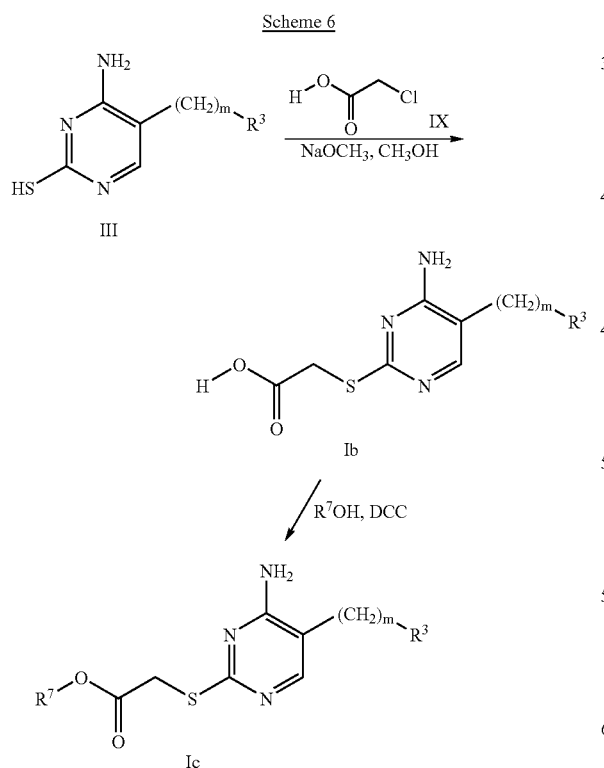

Compounds of formula I, wherein R⁴ signifies $C_1-C_6$-alkyl are prepared by reacting the amine of formula Ia with an appropriate aldehyde. For example, a compound of formula Id, wherein R⁴ is ethyl, is obtained by the reaction of a compound of formula Ia with acetaldehyde and reduction with sodium cyanoborohydride (scheme 7).

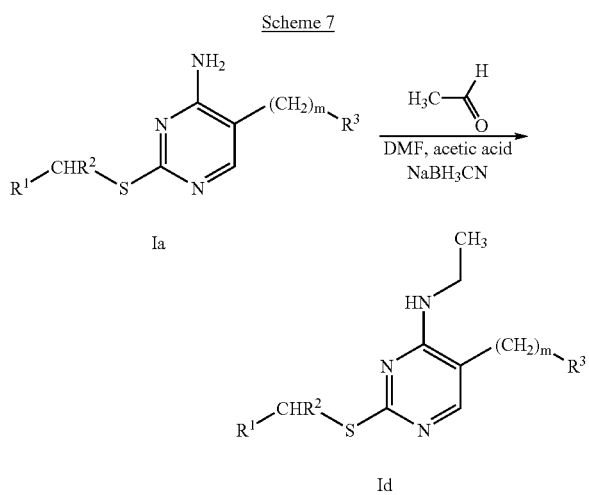

Pharmaceutically acceptable salts of compounds of formula I can be manufactured readily according to methods known to one skilled in the art and taking into consideration the nature of the compound to be converted into a salt. Pharmaceutically acceptable inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The compounds of formula I and their pharmaceutically acceptable salts are, as already mentioned above, metabotropic glutamate receptor antagonists and can be used for the treatment or prevention of mGluR5 receptor mediated disorders, such as acute and/or chronic neurological disorders, cognitive disorders and memory deficits, as well as acute and chronic pain. Treatable neurological disorders are for instance epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method:

cDNA encoding rat mGlu 5a receptor was transiently transfected into EBNA cells using a procedure described by E. -J. Schlaeger and K. Christensen (Cytotechnology 1998, 30, 71–83). [$Ca^{2+}$]i measurements were performed on mGlu 5a transfected EBNA cells after incubation of the cells with Fluo 3-AM (obtainable by FLUKA, 0.5 µM final concentration) for 1 hour at 37° C. followed by 4 washes with assay buffer (DMEM supplemented with Hank's salt and 20 mM HEPES. [$Ca^{2+}$]i measurements were done using a fluorometric imaging plate reader (FLIPR, Molecular Devices Corporation, La Jolla, Calif., USA). When compounds were evaluated as antagonists they were tested against 10 µM glutamate as agonist.

The inhibition (antagonists) curves were fitted with a four parameter logistic equation giving $IC_{50}$, and Hill coefficient using the iterative non linear curve fitting software Origin (Microcal Software Inc., Northampton, Mass., USA).

The compounds of the present invention are mGluR 5a receptor antagonists. The activities of compounds of formula I as measured in the assay described above are in the range of 10 µM or less, typically of 1 µM or less, and ideally of 0.2 µM or less.

In table I below are shown specific activity data of preferred compounds of formula I as measured in the assay described above:

TABLE I

| Example No. | Compound name | $IC_{50}$ (µM) |
| --- | --- | --- |
| 3 | (4-amino-5-benzyl-pyrimidin-2-ylsulfanyl)-acetic acid ethyl ester | 0.14 |
| 4 | [4-amino-5-(1-methyl-1H-pyrrol-2-ylmethyl)-pyrimidin-2-ylsulfanyl]-acetic acid ethyl ester | 0.38 |
| 5 | [4-amino-5-(2,4-dichloro-phenyl)-pyrimidin-2-ylsulfanyl]-acetic acid ethyl ester | 3.85 |
| 6 | [4-amino-5-(4-bromo-benzyl)-pyrimidin-2-ylsulfanyl]-acetic acid ethyl ester | 0.18 |
| 8 | 2-prop-2-ynylsulfanyl-5-thiophen-2-ylmethyl-pyrimidin-4-ylamine | 1.39 |
| 9 | 2-allylsulfanyl-5-thiophen-2-ylmethyl-pyrimidin-4-ylamine | 2.79 |
| 11 | 2-([1,2,4]oxadiazol-3-ylmethylsulfanyl)-5-thiophen-2-ylmethyl-pyrimidin-4-ylamine | 0.4 |
| 12 | (4-amino-5-thiophen-3-ylmethyl-pyrimidin-2-ylsulfanyl)-acetic acid ethyl ester | 0.18 |
| 13 | (4-amino-5-furan-3-ylmethyl-pyrimidin-2-ylsulfanyl)-acetic acid ethyl ester | 0.16 |
| 19 | 4-amino-2-ethoxycarbonylmethylsulfanyl-pyrimidine-5-carboxylic acid ethyl ester | 0.27 |
| 21 | (4-ethylamino-5-thiophen-2-ylmethyl-pyrimidin-2-ylsulfanyl)-acetic acid ethyl ester | 0.6 |
| 22 | (4-amino-5-benzyl-pyrimidin-2-ylsulfanyl)-acetic acid allyl ester | 0.12 |
| 24 | (4-amino-5-benzyl-pyrimidin-2-ylsulfanyl)-acetic acid 2-methyl-cyclopropylmethyl ester | 0.63 |
| 25 | (4-amino-5-benzyl-pyrimidin-2-ylsulfanyl)-acetic acid cyclobutylmethyl ester | 1.46 |
| 29 | (4-amino-5-benzyl-pyrimidin-2-ylsulfanyl)-acetic acid cyclopropylmethyl ester | 0.2 |
| 31 | 4-isobutylamino-5-thiophen-2-ylmethyl-pyrimidin-2-ylsulfanyl)-acetic acid ethyl ester | 0.16 |
| 32 | 5-benzyl-2-(3-cyclopropyl-[1,2,4]oxadiazol-5-ylmethylsulfanyl)-pyrimidin-4-ylamine | 0.45 |

The compounds of formula I and pharmaceutically acceptable salts thereof can be used as pharmaceutical compositions. The pharmaceutical compositions can be administered orally, e.g. in the form of tablets, coated tablets, dragées, hard and soft gelatin capsules, solutions, emulsions or suspensions. However, the administration can also be effected rectally, e.g. in the form of suppositories, or parenterally, e.g. in the form of injection solutions.

A therapeutically effective amount of the compounds of formula I and pharmaceutically acceptable salts thereof can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, pharmaceutical compositions containing a compound of formula IA or IB or pharmaceutically acceptable salts thereof and a therapeutically inert excipient are also an object of the present invention, as is a process for the production of such pharmaceutical compositions which comprises bringing a therapeutically effective amount of one or more compounds of formula IA or IB or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

EXAMPLES

General Procedure A

Synthesis of 2-substituted 3-phenylamino-acrylonitriles

Potassium-tert-butylate (1 eq.) is added to a cooled (10° C.) solution of 3-phenylamino-propionitrile (1 eq.) and an aldehyde (1 eq.) in DMSO (approx. 0.3M). After stirring for 3 hours at r.t., the mixture is cooled in an ice bath and water is added. The mixture is extracted several times with diethylether, the combined organic phases are dried over $MgSO_4$, and most of the solvent is evaporated under reduced pressure. The 2-substituted 3-phenylamino-acrylonitrile crystallizes from the remaining solvent and is sufficiently pure for further conversion according to general procedure B.

General Procedure B

Synthesis of 5-substituted 4-amino-pyrimidine-2-thiols

A catalytic amount (e.g. 0.1 eq.) of sodium ethoxide is added to a solution of 2-substituted 3-phenylamino-acrylonitrile (1 eq.) as prepared according to general procedure A and thiourea (1.1 eq.) in ethanol which is then heated to reflux. After 6 h, a drop of formic acid is added and approximately half of the solvent is evaporated under reduced pressure. The mixture is then placed in a refrigerator (4° C.) overnight. The precipitated 5-substituted 4-amino-pyrimidine-2-thiol is collected and purified, e.g. by crystallisation from EtOH or by column chromatography.

General Procedure C

Synthesis of 5-substituted 2-Alkylsulfanyl-pyrimidin-4-ylamines 5-substituted 4-amino-pyrimidine-2-thiol is dissolved in 1M sodium methoxide solution in methanol or IM sodium ethoxide solution in ethanol (1 eq.). After addition of an alkyl halide (2 eq.), the mixture is stirred for 90 min at r.t. Formic acid (1 eq.) is added and the 5-substituted 2-alkylsulfanyl-pyrimidin-4-ylamine is isolated from the mixture, e.g. by HPLC chromatography (YMC CombiPrep C18 column 50×20 mm, solvent gradient 10–95% $CH_3CN$ in 0.1% TFA(aq) over 6.0 min, λ=230 nm, flow rate 40 ml/min).

Unless stated to the contrary, all of the examples listed below were prepared and characterized as described.

Example 1

(4-Amino-5-thiophen-2-ylmethyl-pyrimidin-2-ylsulfanyl)-acetic acid methyl ester

Following general procedures A, B, and C, the title compound, MS: m/e=295.7 $(M+H^+)$, was prepared using 2-thiophenecarbaldehyde and methyl bromoacetate.

Example 2

(4-Amino-5-thiophen-2-ylmethyl-pyrimidin-2-ylsulfanyl)-acetic acid ethyl ester

Following general procedures A, B, and C, the title compound, MS: m/e=309.7 $(M+H^+)$, was prepared using 2-thiophenecarbaldehyde and ethyl bromoacetate.

Example 3

(4-Amino-5-benzyl-pyrimidin-2-ylsulfanyl)-acetic acid ethyl ester

Following general procedures A, B, and C, the title compound, MS: m/e=303.8 $(M+H^+)$, was prepared using benzaldehyde and ethyl bromoacetate.

Example 4

[4-Amino-5-(1-methyl-1H-pyrrol-2-ylmethyl)-pyrimidin-2-ylsulfanyl]-acetic acid ethyl ester Following general procedures A, B, and C, the title compound, MS: m/e=306.8 $(M+H^+)$, was prepared using 1-methylpyrrole-2-carboxaldehyde and ethyl bromoacetate.

Example 5

[4-Amino-5-(2,4-dichloro-phenyl)-pyrimidin-2-yl-sulfanyl]-acetic acid ethyl ester 2-(2,4-Dichloro-phenyl)-3-piperidin-1-yl-acrylonitrile 2-(2,4-Dichloro-phenyl)-3-piperidin-1-yl-acrylonitrile was prepared according to the method as described in *Tetrahedron* 1972, 28, 1343.

[4-Amino-5-(2,4-dichloro-phenyl)-pyrimidin-2-yl-sulfanyl]-acetic acid ethyl ester Following general procedures B and C, the title compound, MS: m/e=358.0 $(M+H^+)$, was prepared using 2-(2,4-dichloro-phenyl)-3-piperidin-1-yl-acrylonitrile and ethyl bromoacetate.

Example 6

[4-Amino-5-(4-bromo-benzyl)-pyrimidin-2-ylsulfanyl]-acetic acid ethyl ester

Following general procedures A, B, and C, the title compound, MS: m/e=382.0 $(M+H^+)$, was prepared using 4-bromobenzaldehyde and ethyl bromoacetate.

Example 7

2-(4-Amino-5-thiophen-2-ylmethyl-pyrimidin-2-ylsulfanyl)-propionic acid methyl ester Following general procedures A, B, and C, the title compound, MS: m/e=310.2 $(M+H^+)$, was prepared using 2-thiophenecarbaldehyde and 2-bromo-propionic acid methyl ester.

Example 8

2-Prop-2-ynylsulfanyl-5-thiophen-2-ylmethyl-pyrimidin-4-ylamine

Following general procedures A, B, and C, the title compound, MS: m/e=262.0 $(M+H^°)$, was prepared using 2-thiophenecarbaldehyde and propargyl bromide.

Example 9

2-Allylsulfanyl-5-thiophen-2-ylmethyl-pyrimidin-4-ylamine

Following general procedures A, B, and C, the title compound, MS: m/e=264.0 $(M+H^+)$, was prepared using 2-thiophenecarbaldehyde and allyl bromide.

Example 10

2-Cyclopropylmethylsulfanyl-5-thiophen-2-ylmethyl-pyrimidin-4-ylamine

Following general procedures A, B, and C, the title compound, MS: m/e=278.0 $(M+H^+)$, was prepared using 2-thiophenecarbaldehyde and bromomethyl-cyclopropane.

Example 11

2-([1,2,4]Oxadiazol-3-ylmethylsulfanyl)-5-thiophen-2-ylmethyl-pyrimidin-4-ylamine Following general procedures A, B, and C, the title compound, MS: m/e=306.0 (M+H$^+$), was prepared using 2-thiophenecarbaldehyde and 3-chloromethyl-[1,2,4]oxadiazole.

Example 12

(4-Amino-5-thiophen-3-ylmethyl-pyrimidin-2-ylsulfanyl)-acetic acid ethyl ester

Following general procedures A, B, and C, the title compound, MS: m/e=310.0 (M+H$^+$), was prepared using 3-thiophenecarbaldehyde and ethyl bromoacetate.

Example 13

(4-Amino-5-furan-3-ylmethyl-pyrimidin-2-ylsulfanyl)-acetic acid ethyl ester

Following general procedures A, B, and C, the title compound, MS: m/e=294.0 (M+H$^+$), was prepared using 3-furancarbaldehyde and ethyl bromoacetate.

Example 14

[4-Amino-5-(3-methyl-thiophen-2-ylmethyl)-pyrimidin-2-ylsulfanyl]-acetic acid ethyl ester Following general procedures A, B, and C, the title compound, MS: m/e=324.0 (M+H$^+$), was prepared using 3-methyl-thiophene-2-carbaldehyde and ethyl bromoacetate.

Example 15

[4-Amino-5-(5-chloro-thiophen-2-ylmethyl)-pyrimidin-2-ylsulfanyl]-acetic acid ethyl ester Following general procedures A, B, and C, the title compound, MS: m/e=344.0 (M+H$^+$), was prepared using 5-chloro-thiophene-2-carbaldehyde and ethyl bromoacetate.

Example 16

[4-Amino-5-(5-ethyl-furan-2-ylmethyl)-pyrimidin-2-ylsulfanyl]-acetic acid ethyl ester Following general procedures A, B, and C, the title compound, MS: m/e=322.0 (M+H$^+$), was prepared using 5-ethyl-furan-2-carbaldehyde and ethyl bromoacetate.

Example 17

[4-Amino-5-(5-methyl-furan-2-ylmethyl)-pyrimidin-2-ylsulfanyl]-acetic acid ethyl ester Following general procedures A, B, and C, the title compound, MS: m/e=308.0 (M+H$^+$), was prepared using 5-methyl-furan-2-carbaldehyde and ethyl bromoacetate.

Example 18

4-(2-Allylsulfanyl-4-amino-pyrimidin-5-ylmethyl)-benzonitrile

Following general procedures A, B, and C, the title compound, MS: m/e=283.0 (M+H$^+$), was prepared using 4-formyl-benzonitrile and allyl bromide.

Example 19

4-Amino-2-ethoxycarbonylmethylsulfanyl-pyrimidine-5-carboxylic acid ethyl ester

Following general procedures B and C, the title compound, MS: m/e=286.0 (M+H$^+$), was prepared using ethyl 2-cyano-3-(3-thienylamino)-acrylate and ethyl bromoacetate.

Example 20

[4-Amino-5-(2-chloro-phenyl)-pyrimidin-2-ylsulfanyl]-acetic acid ethyl ester a) 2-(2-Chloro-phenyl)-3-piperidin-1-yl-acrylonitrile 2-(2-Chloro-phenyl)-3-piperidin-1-yl-acrylonitrile was prepared in analogy to the method as described in Tetrahedron 1972, 28, 1343.

b) [4-Amino-5-(2-chloro-phenyl)-pyrimidin-2-ylsulfanyl]-acetic acid ethyl ester

Following general procedures B and C, the title compound, MS: m/e=324.0 (M+H$^+$), was prepared using 2-(2-chloro-phenyl)-3-piperidin-1-yl-acrylonitrile and ethyl bromoacetate.

Example 21

(4-Ethylamino-5-thiophen-2-ylmethyl-pyrimidin-2-ylsulfanyl)-acetic acid ethyl ester To a solution of (4-Amino-5-thiophen-2-ylmethyl-pyrimidin-2-ylsulfanyl)-acetic acid ethyl ester (0.5 mmol, 155 mg) as prepared in example 12 and acetaldehyde (0.6 mmol, 27 mg) in 1.25 ml of DMF was added acetic acid (0.25 ml) and sodium cyanoborohydride (0.6 mmol, 38 mg) and the mixture was shaken for two days at r.t. The title compound, MS: m/e=338.2 (M+H$^+$), was obtained from the mixture by HPLC chromatography (YMC CombiPrep C18 column 50×20 mm, solvent gradient 10–95% CH$_3$CN in 0.1% TFA(aq) over 6.0 min, λ=230 nm, flow rate 40 ml/min).

Example 22

(4-Amino-5-benzyl-pyrimidin-2-ylsulfanyl)-acetic acid allyl ester a) (4-Amino-5-benzyl-pyrimidin-2-ylsulfanyl)-acetic acid (4-Amino-5-benzyl-pyrimidin-2-ylsulfanyl)-acetic acid was obtained from 4-amino-5-benzyl-pyrimidine-2-thiol in analogy to the method in *J. Org. Chem.* 1956, 21, 567. 4-Amino-5-benzyl-pyrimidine-2-thiol was prepared according to general procedures A and B using benzaldehyde.

b) (4-Amino-5-benzyl-pyrimidin-2-ylsulfanyl)-acetic acid allyl ester (4-Amino-5-benzyl-pyrimidin-2-ylsulfanyl)-acetic acid (0.25 mmol, 69 mg), dicyclohexylcarbodiimide (0.3 mmol, 62 mg) and allyl alcohol (0.3 mmol, 18 mg) were dissolved in 1 ml of DMF, and a catalytic amount of 4-dimethylaminopyridine (approx. 1–3 mg) was added. After shaking the mixture for 24 h at r.t., the title compound, MS: m/e=316.2 (M+H$^+$), was obtained from the reaction mixture by HPLC chromatography (YMC CombiPrep C18 column 50×20 mm, solvent gradient 10–95% CH$_3$CN in 0.1% TFA(aq) over 6.0 min, λ=230 nm, flow rate 40 ml/min).

Example 23

(4-Amino-5-benzyl-pyrimidin-2-ylsulfanyl)-acetic acid prop-2-ynyl ester

The title compound, MS: m/e=314.0 (M+H$^+$), was prepared from propargyl alcohol in analogy to the method described in example 22.

Example 24

(4-Amino-5-benzyl-pyrimidin-2-ylsulfanyl)-acetic acid 2-methyl-cyclopropylmethyl ester The title compound, MS: m/e=343.9 (M+H$^+$), was prepared from (2-methyl-cyclopropyl)-methanol in analogy to the method described in example 22.

Example 25

(4-Amino-5-benzyl-pyrimidin-2-ylsulfanyl)-acetic acid cyclobutylmethyl ester a) Cyclobutylmethanol Cyclobutylmethanol was prepared according to the method as described in *J. Chem. Soc. Perkin Trans.* 1; 1993; 7, 801–804.

b) 4-Amino-5-benzyl-pyrimidin-2-ylsulfanyl)-acetic acid cyclobutylmethyl ester

The title compound, MS: m/e=343.9 (M+H$^+$), was prepared from cyclobutylmethanol in analogy to the method described in example 22.

Example 26

(4-Amino-5-benzyl-pyrimidin-2-ylsulfanyl)-acetic acid cyclobutyl ester

The title compound, MS: m/e=330.0 (M+H$^+$), was prepared from cyclobutanol in analogy to the method described in example 22.

Example 27

(4-Amino-5-benzyl-pyrimidin-2-ylsulfanyl)-acetic acid cyclopentyl ester

The title compound, MS: m/e=344.0 (M+H$^+$), was prepared from cyclopentanol in analogy to the method described in example 22.

Example 28

(4-Amino-5-benzyl-pyrimidin-2-ylsulfanyl)-acetic acid 5-methyl-isoxazol-3-ylmethyl ester The title compound, MS: m/e=371.0 (M+H$^+$), was prepared from (5-Methyl-isoxazol-3-yl)-methanol in analogy to the method described in example 22.

Example 29

(4-Amino-5-benzyl-pyrimidin-2-ylsulfanyl)-acetic acid cyclopropylmethyl ester

The title compound, MS: m/e=330.0 (M+H$^+$), was prepared from cyclopropylmethanol in analogy to the method described in example 22.

Example 30

(4-Amino-5-benzyl-pyrimidin-2-yloxy)-acetic acid methyl ester

Following general procedures A, B, and C, the title compound, MS: m/e=274.0 (M+H$^+$), was prepared using benzaldehyde and methyl bromoacetate.

Example 31

4-Isobutylamino-5-thiophen-2-ylmethyl-pyrimidin-2-ylsulfanyl)-acetic acid ethyl ester The title compound, MS: m/e=366.0 (M+H$^+$), was prepared in analogy to the method of example 21 from isobutyraldehyde.

Example 32

(4-Amino-5-cyclopropylmethyl-pyrimidin-2-ylsulfanyl)-acetic acid ethyl ester

Following general procedures A, B, and C, the title compound, MS: m/e=267.9 (M+H$^+$), was prepared using cyclopropylcarbaldehyde and ethyl bromoacetate.

Example 33

5-Benzyl-2-(3-cyclopropyl-[1,2,4]oxadiazol-5-ylmethylsulfanyl)-pyrimidin-4-ylamine A solution of (4-amino-5-benzyl-pyrimidin-2-ylsulfanyl)-acetic acid (0.35 mg, 1.27 mmol) as prepared according to the method described in example 22, and 1,1'-carbonyldiimidazole (0.31 g, 1.91 mmol) in DMF (8 ml) was stirred at room temperature for 3 h and subsequently N-hydroxycyclopropanecarboxamidine (0.19 g, 1.91 mmol) was added. The reaction mixture was stirred at 80° C. for 20 h and evaporated. Acetic acid (10 ml) was added and the stirred mixture was heated under reflux conditions for 2 h. Aqueous work-up, column chromatography on silica gel (ethyl acetate/hexane 3:2) and crystallization from ethyl acetate/hexane yielded the title compound (36 mg, 9%) as an off-white solid, m.p. 94° C. and MS: m/e=340.3 (M+H$^+$).

Example A

Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example B

Tablets of the following composition are produced in a conventional manner:

| | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example C

Capsules of the following composition are produced:

| | mg/Capsule |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another; sieved and thereafter talc and magnesium stearate are admixed. The final mixture is filled into hard gelatin capsules of suitable size.

The invention claimed is:

1. A compound of formula I

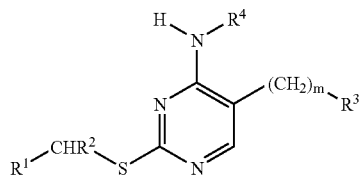

wherein $R^1$ is selected from the group consisting of $C_2$–$C_6$-alkenyl,
$C_2$–$C_6$-alkinyl,
$C_3$–$C_6$-unsubstituted cycloalkyl,
—C(O)O—($C_1$–$C_6$)-alkyl,
—C(O)O—($C_2$–$C_6$)-alkenyl,
—C(O)O—($C_2$–$C_6$)-alkinyl,
—C(O)O—($C_3$–$C_6$)-unsubstituted cycloalkyl
—C(O)O—$CH_2$-unsubstituted ($C_3$–$C_6$)-cycloalkyl,
—C(O)O—($C_3$–$C_6$)-cycloalkyl substituted by at least one unsubstituted heteroaryl,
—C(O)O—$CH_2$—($C_3$–$C_6$)-cycloalkyl substituted by at least one unsubstituted heteroaryl, and
—C(O)O—$CH_2$-heteroaryl substituted by a substituent selected from the group consisting of
at least one $C_1$–$C_6$-alkyl,
unsubstituted heteroaryl, and heteroaryl substituted by at least one substituent selected from the group consisting of
$C_1$–$C_6$-alkyl, $C_2$–$C_6$-alkenyl, $C_2$–$C_6$-alkinyl, $C_3$–$C_6$-cycloalkyl and halogen;

$R^2$ selected group is from the consisting of hydrogen and $C_1$–$C_6$-alkyl;

$R^3$ is unsubstituted heteroaryl or heteroaryl substituted by at least one substituent selected from the group selected from $C_1$–$C_6$-alkyl, $C_2$–$C_6$-alkenyl, $C_2$–$C_6$-alkinyl, $C_3$–$C_6$-cycloalkyl, halogen and cyano;

$R^4$ is selected from the group consisting of hydrogen and $C_1$–$C_6$-alkyl; and m is 0, 1 or 2;

or a pharmaceutically acceptable salt thereof.

2. A compound of formula I, according to claim 1, wherein $R^1$ is selected from the group consisting of
—C(O)O—($C_1$–$C_6$)-alkyl, —C(O)O—($C_2$–$C_6$)-alkenyl, —C(O)O—($C_2$–$C_6$)-alkinyl, —C(O)O—($C_3$–$C_6$)-cycloalkyl, —C(O)O—$CH_2$—($C_3$–$C_6$)-cycloalkyl, —C(O)O—($C_3$–$C_6$)-cycloalkyl or —C(O)O—$CH_2$—($C_3$–$C_6$)-cycloalkyl substituted by at least one $C_1$–$C_6$-alkyl, —C(O)O—$CH_2$-heteroaryl and C(O)O—$CH_2$-heteroaryl substituted by at least one $C_1$–$C_6$-alkyl.

3. A compound of formula I, according to claim 2, selected from the group consisting of
(4-amino-5-thiophen-2-ylmethyl-pyrimidin-2-ylsulfanyl)-acetic acid methyl ester, (4-amino-5-thiophen-2-ylmethyl-pyrimidin-2-ylsulfanyl)-acetic acid ethyl ester, [4-amino-5-(1-methyl-1H-pyrrol-2-ylmethyl)-pyrimidin-2-ylsulfanyl]-acetic acid ethyl ester, 2-(4-amino-5-thiophen-2-ylmethyl-pyrimidin-2-ylsulfanyl)-propionic acid methyl ester, (4-amino-5-thiophen-3-ylmethyl-pyrimidin-2-ylsulfanyl)-acetic acid ethyl ester, (4-amino-5-furan-3-ylmethyl-pyrimidin-2-ylsulfanyl)-acetic acid ethyl ester, [4-amino-5-(3-methyl-thiophen-2-ylmethyl)-pyrimidin-2-ylsulfanyl]-acetic acid ethyl ester, [4-amino-5-(5-chloro-thiophen-2-ylmethyl)-pyrimidin-2-ylsulfanyl]-acetic acid ethyl ester, [4-amino-5-(5-ethyl-furan-2-ylmethyl)-pyrimidin-2-ylsulfanyl]-acetic acid ethyl ester, [4-amino-5-(5-methyl-furan-2-ylmethyl)-pyrimidin-2-ylsulfanyl]-acetic acid ethyl ester, (4-ethylamino-5-thiophen-2-ylmethyl-pyrimidin-2-ylsulfanyl)-acetic acid ethyl ester, and (4-isobutylamino-5-thiophen-2-ylmethyl-pyrimidin-2-ylsulfanyl)-acetic acid ethyl ester.

4. A compound of formula I, according to claim 1, wherein $R^1$ is unsubstituted heteroaryl or heteroaryl substituted by at least one substituent selected from the group consisting of $C_1$–$C_6$-alkyl, $C_2$–$C_6$-alkenyl, $C_2$–$C_6$-alkinyl, $C_3$–$C_6$-cycloalkyl or halogen.

5. A compound of formula I, according to claim 4, which is 2-([1,2,4]oxadiazol-3-ylmethylsulfanyl)-5-thiophen-2-yl-methyl-pyrimidin-4-ylamine.

6. A compound of formula I, according to claim 1, wherein $R^1$ is selected from the group consisting of $C_2$–$C_6$-alkenyl, $C_2$–$C_6$-alkinyl and $C_3$–$C_6$-cycloalkyl.

7. A compound of formula I, according to claim 6, selected from the group consisting of
2-prop-2-ynylsulfanyl-5-thiophen-2-ylmethyl-pyrimidin-4-ylamine,
2-allylsulfanyl-5-thiophen-2-ylmethyl-pyrimidin-4-ylamine, and
2-cyclopropylmethylsulfanyl-5-thiophen-2-ylmethyl-pyrimidin-4-ylamine.

8. A pharmaceutical composition comprising a therapeutically effective amount of at least one compound of formula I, according to claim 1, and at least one pharmaceutically acceptable excipient.

9. A compound of formula I

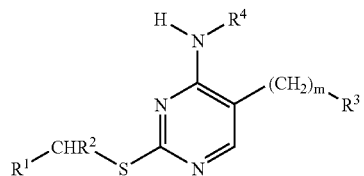

wherein
$R^1$ is heteroaryl substituted by at least one substituent selected from the group consisting of $C_2$–$C_6$-alkinyl, $C_3$–$C_6$-cycloalkyl and halogen;
$R^2$ is selected from the group consisting of hydrogen and $C_1$–$C_6$-alkyl;
$R^3$ is aryl substituted by at least one substituent selected from the group consisting of $C_1$–$C_6$-alkyl, $C_2$–$C_6$-alkinyl, $C_3$–$C_6$-cycloalkyl, halogen and cyano;
$R^4$ is selected from the group consisting of hydrogen and $C_1$–$C_6$-alkyl; and
m is 0, 1 or 2;
or a pharmaceutically acceptable salt thereof.

10. A pharmaceutical composition comprising a therapeutically effective amount of at least one compound of formula I, according to claim 9, and at least one pharmaceutically acceptable excipient.

11. The compound 5-benzyl-2-(3-cyclopropyl-[1,2,4]oxadiazol-5-ylmethylsulfanyl)-pyrimidin-4-ylamine.

12. A compound of formula I,

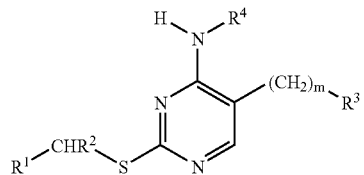

wherein
$R^1$ is $C_3$–$C_6$-cycloalkyl;
$R^2$ is selected from the group consisting of hydrogen and $C_1$–$C_6$-alkyl;
$R^3$ is selected from the group consisting of
unsubstituted aryl,
aryl substituted by at least one substituent selected from the group consisting of
$C_1$–$C_6$-alkyl, $C_2$–$C_6$-alkenyl, $C_2$–$C_6$-alkinyl, $C_3$–$C_6$-cycloalkyl, halogen, cyano, unsubstituted heteroaryl and
$C_1$–$C_6$-alkyl, $C_2$–$C_6$-alkenyl, $C_2$–$C_6$-alkinyl, $C_3$–$C_6$-cycloalkyl, halogen, cyano, and
—C(O)O—($C_1$–$C_6$)-alkyl;
$R^4$ is selected from the group consisting of hydrogen and $C_1$–$C_6$-alkyl; and
m is 0, 1 or 2;
or a pharmaceutically acceptable salt thereof, to a patient in need of such treatment.

13. A pharmaceutical composition comprising a therapeutically effective amount of at least one compound of formula I, according to claim 12, and at least one pharmaceutically acceptable excipient.

14. The compound 4-(2-allylsulfanyl-4-amino-pyrimidin-5-ylmethyl)-benzonitrile.

15. A compound of formula I,

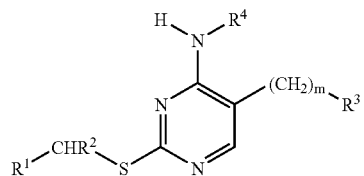

wherein
$R^1$ is selected from the group consisting of $C_2$–$C_6$-alkenyl,
$C_3$–$C_6$-unsubstituted cycloalkyl,
—C(O)O—($C_1$–$C_6$)-alkyl,
—C(O)O—($C_2$–$C_6$)-alkenyl,
—C(O)O—($C_2$–$C_6$)-alkinyl,
—C(O)O—($C_3$–$C_6$)-unsubstituted cycloalkyl
—C(O)O—$CH_2$-unsubstituted ($C_3$–$C_6$)-cycloalkyl,
—C(O)O—($C_3$–$C_6$)-cycloalkyl substituted by at least one unsubstituted heteroaryl,
—C(O)O—$CH_2$—($C_3$–$C_6$)-cycloalkyl substituted by at least one unsubstituted heteroaryl, and
—C(O)O—$CH_2$-heteroaryl substituted by a substituent selected from the group consisting of
at least one $C_1$–$C_6$-alkyl,
unsubstituted heteroaryl, and heteroaryl substituted by at least one substituent selected from the group consisting of
$C_1$–$C_6$-alkyl, $C_2$–$C_6$-alkenyl, $C_2$–$C_6$-alkinyl, $C_1$–$C_6$-cycloalkyl and halogen;
$R^2$ is selected from the group consisting of hydrogen and $C_1$–$C_6$-alkyl;
$R^3$ is $C_3$–$C_6$-cycloalkyl;
$R^4$ is selected from the group consisting of hydrogen and $C_1$–$C_6$-alkyl; and
m is 0, 1 or 2;
or a pharmaceutically acceptable salt thereof.

16. A pharmaceutical composition comprising a therapeutically effective amount of at least one compound of formula I, according to claim 15, and at least one pharmaceutically acceptable excipient.

17. The compound (4-amino-5-cyclopropylmethyl-pyrimidin-2-ylsulfanyl)-acetic acid ethyl ester.

18. A compound of formula I, wherein
$R^1$ selected from the group consisting of
- —C(O)O—($C_1$–$C_6$)-alkyl,
- —C(O)O—($C_2$–$C_6$)-alkenyl,
- —C(O)O—($C_2$–$C_6$)-alkinyl,
- —C(O)O—($C_3$–$C_6$)-unsubstituted cycloalkyl,
- —C(O)O—$CH_2$—($C_3$–$C_6$)-unsubstituted cycloalkyl,
- —C(O)O—($C_3$–$C_6$)-cycloalkyl substituted by at least one $C_1$–$C_6$-alkyl,
- —C(O)O—$CH_2$—($C_3$–$C_6$)-cycloalkyl substituted by at least one $C_1$–$C_6$-alkyl,
- —C(O)O—$CH_2$-heteroaryl and
- —C(O)O—$CH_2$-heteroaryl substituted by at least one $C_1$–$C_6$-alkyl;

$R_2$ is selected from the group consisting of hydrogen and $C_1$–$C_6$-alkyl;

$R^3$ is selected from the group consisting of
- unsubstituted aryl,
- aryl substituted by at least one substituent selected from the group consisting of
  $C_1$–$C_6$-alkyl, $C_2$–$C_6$-alkenyl, $C_2$–$C_6$-alkinyl, $C_3$–$C_6$-cycloalkyl, halogen, cyano, unsubstituted heteroaryl and
- heteroaryl substituted by at least one substituent selected from the group consisting of
  $C_1$–$C_6$-alkyl, $C_2$–$C_6$-alkenyl, $C_2$–$C_6$-alkinyl, $C_3$–$C_6$-cycloalkyl, halogen, cyano, and
  —C(O)O—($C_1$–$C_6$)-alkyl;

$R_4$ is selected from the group consisting of hydrogen and $C_1$–$C_6$-alkyl; and m is 0;

or a pharmaceutically acceptable salt thereof.

19. A compound of formula 1, according to claim 18, selected from the group consisting of
[4-amino-5-(2,4-dichloro-phenyl)-pyrimidin-2-ylsulfanyl]-acetic acid ethyl ester, 4-amino-2-ethoxycarbonylmethylsulfanyl-pyrimidine-5-carboxylic acid ethyl ester, and [4-amino-5-(2-chloro-phenyl)-pyrimidin-2-ylsulfanyl]-acetic acid ethyl ester.

20. A pharmaceutical composition comprising a therapeutically effective amount of at least one compound of formula I, according to claim 18, and at least one pharmaceutically acceptable excipient.

21. A process for the manufacture of a compound of formula I wherein
$R^1$ is selected from the group consisting of $C_2$–$C_6$-alkenyl,
- $C_2$–$C_6$-alkinyl,
- $C_3$–$C_6$-unsubstituted cycloalkyl,
- —C(O)O—($C_1$–$C_6$)-alkyl,
- —C(O)O—($C_2$–$C_6$)-alkenyl,
- —C(O)O—($C_2$–$C_6$)-alkinyl,
- —C(O)O—($C_3$–$C_6$)-unsubstituted cycloalkyl
- —C(O)O—$CH_2$-unsubstituted ($C_3$–$C_6$)-cycloalkyl,
- —C(O)O—($C_3$–$C_6$)-cycloalkyl substituted by at least one unsubstituted heteroaryl,
- —C(O)O—$CH_2$-($C_3$–$C_6$)-cycloalkyl substituted by at least one unsubstituted heteroaryl, and
- —C(O)O—$CH_2$-heteroaryl substituted by a substituent selected from the group consisting of
  at least one $C_1$–$C_6$-alkyl,
  unsubstituted heteroaryl, and heteroaryl substituted by at least one substituent selected from the group consisting of
  $C_1$–$C_6$-alkyl, $C_2$–$C_6$-alkenyl, $C_2$–$C_6$-alkinyl, $C_3$–$C_6$-cycloalkyl and halogen;

$R^2$ is selected from the group consisting of hydrogen and $C_1$–$C_6$-alkyl;

$R^3$ is selected from the group consisting of
- unsubstituted aryl,
- aryl substituted by at least one substituent selected from the group consisting of
  $C_1$–$C_6$-alkyl, $C_2$–$C_6$-alkenyl, $C_2$–$C_6$-alkinyl, $C_3$–$C_6$-cycloalkyl, halogen, cyano,
- unsubstituted heteroaryl and
- heteroaryl substituted by at least one substituent selected from the group consisting of
  $C_1$–$C_6$-alkyl, $C_2$–$C_6$-alkenyl, $C_2$–$C_6$-alkinyl, $C_3$–$C_6$-cycloalkyl, halogen, cyano, and
  —(O)O—($C_1$–$C_6$)-alkyl;

$R^4$ is selected from the group consisting of hydrogen and $C_1$–$C_6$-alkyl; and m is 0, 1 or 2;

or a pharmaceutically acceptable salt thereof, comprising reacting a compound of formula wherein
$R^5$ is selected from the group consisting of phenylamino, 3-thienylamino and morpholino, with thiourea forming a compound of formula

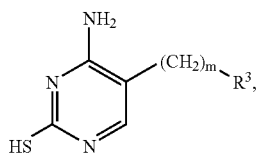

reacting this compound with a compound of formula

wherein X is halogen,
converting the amino group into an aminoalkyl group, thereby forming a compound of formula

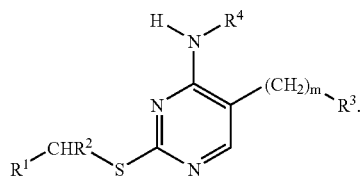

22. A method for the treatment of anxiety comprising administering a therapeutically effective amount of a compound of formula I

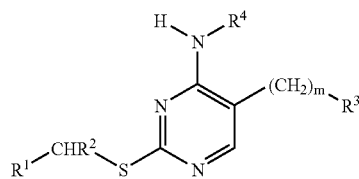

wherein
$R^1$ is selected from the group consisting of $C_2$–$C_6$-alkenyl,
$C_2$–$C_6$-alkinyl,
$C_3$–$C_6$-unsubstituted cycloalkyl,
—C(O)O—($C_1$–$C_6$)-alkyl,
—C(O)O—($C_2$–$C_6$)-alkenyl,
—C(O)O—($C_2$–$C_6$)-alkinyl,
—C(O)O—($C_3$–$C_6$)-unsubstituted cycloalkyl
—C(O)O—$CH_2$-unsubstituted ($C_3$–$C_6$)-cycloalkyl,
—C(O)O—($C_3$–$C_6$)-cycloalkyl substituted by at least one unsubstituted heteroaryl,
—C(O)O—$CH_2$—($C_3$–$C_6$)-cycloalkyl substituted by at least one unsubstituted heteroaryl, and
—C(O)O—$CH_2$-heteroaryl substituted by a substituent selected from the group consisting of
at least one $C_1$–$C_6$-alkyl,
unsubstituted heteroaryl, and heteroaryl substituted by at least one substituent selected from the group consisting of
$C_1$–$C_6$-alkyl, $C_2$–$C_6$-alkenyl, $C_2$–$C_6$-alkinyl, $C_3$–$C_6$-cycloalkyl and halogen;
$R^2$ selected group is from the consisting of hydrogen and $C_1$–$C_6$-alkyl;
$R^3$ is selected from the group consisting of
unsubstituted aryl,
aryl substituted by at least one substituent selected from the group consisting of
$C_1$–$C_6$-alkyl, $C_2$–$C_6$-alkenyl, $C_2$–$C_6$-alkinyl, $C_3$–$C_6$-cycloalkyl, halogen, cyano,
unsubstituted heteroaryl and
heteroaryl substituted by at least one substituent selected from the group consisting of
$C_1$–$C_6$-alkyl, $C_2$–$C_6$-alkenyl, $C_2$–$C_6$-alkinyl, $C_3$–$C_6$-cycloalkyl, halogen, cyano, and
—(O)O—($C_1$–$C_6$)-alkyl;
$R^4$ is selected from the group consisting of hydrogen and $C_1$–$C_6$-alkyl; and
m is 0, 1 or 2;
or a pharmaceutically acceptable salt thereof, to a patient in need of such treatment.

23. A method for the treatment of chronic and acute pain comprising administering a therapeutically effective amount of a compound of formula I,

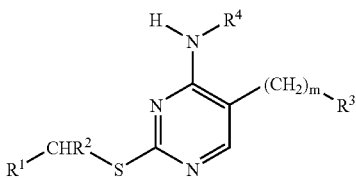

wherein
$R^1$ is selected from the group consisting of $C_2$–$C_6$-alkenyl,
$C_2C_6$alkinyl,
$C_3$–$C_6$-unsubstituted cycloalkyl,
—C(O)O—($C_1$–$C_6$)-alkyl,
—C(O)O—($C_2$–$C_6$)-alkenyl,
—C(O)O—($C_2$–$C_6$)-alkinyl,
—C(O)O—($C_3$–$C_6$)-unsubstituted cycloalkyl
—C(O)O—$CH_2$-unsubstituted ($C_3$–$C_6$)-cycloalkyl,
—C(O)O—($C_3$–$C_6$)-cycloalkyl substituted by at least one unsubstituted heteroaryl,
—C(O)O—$CH_2$-($C_3$–$C_6$)-cycloalkyl substituted by at least one unsubstituted heteroaryl, and
—C(O)O—$CH_2$-heteroaryl substituted by a substituent selected from the group consisting of
at least one $C_1$–$C_6$-alkyl,
unsubstituted heteroaryl, and heteroaryl substituted by at least one substituent selected from the group consisting of
$C_1$–$C_6$-alkyl, $C_2$–$C_6$-alkenyl, $C_2$–$C_6$-alkinyl, $C_3$–$C_6$-cycloalkyl and halogen;
$R^2$ is selected from the group consisting of hydrogen and $C_1$–$C_6$-alkyl;
$R^3$ is selected from the group consisting of
unsubstituted aryl,
aryl substituted by at least one substituent selected from the group consisting of
$C_1$–$C_6$-alkyl, $C_2$–$C_6$-alkenyl, $C_2$–$C_6$-alkinyl, $C_3$–$C_6$-cycloalkyl, halogen, cyano,
unsubstituted heteroaryl and heteroaryl substituted by at least one substituent selected from the group consisting of
C$_1$–C$_6$-alkyl, C$_2$–C$_6$-alkenyl, C$_2$–C$_6$-alkinyl, C$_3$–C$_6$-cycloalkyl, halogen, cyano, and
—C(O)O—(C$_1$–C$_6$)-alkyl;
R$^4$ is selected from the group consisting of hydrogen and C$_1$–C$_6$-alkyl; and
m is 0, 1 or 2;
or a pharmaceutically acceptable salt thereof, to a patient in need of such treatment.

24. A method for the treatment of urinary incontinence comprising administering a therapeutically effective amount of a compound of formula I,

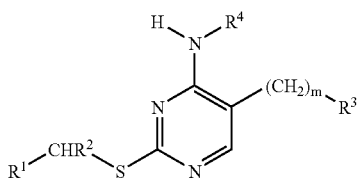

wherein
R$^1$ is selected from the group consisting of C$_2$–C$_6$-alkenyl,
C$_2$–C$_6$alkinyl,
C$_3$–C$_6$-unsubstituted cycloalkyl,
—C(O)O—(C$_1$–C$_6$)-alkyl,
—C(O)O—(C$_2$–C$_6$)-alkenyl,
—C(O)O—(C$_2$–C$_6$)-alkinyl,
—C(O)O—(C$_3$–C$_6$)-unsubstituted cycloalkyl
—C(O)O—CH$_2$-unsubstituted (C$_3$–C$_6$)-cycloalkyl,
—C(O)O—(C$_3$–C$_6$)-cycloalkyl substituted by at least one unsubstituted heteroaryl,
—C(O)O—CH$_2$-(C$_3$–C$_6$)-cycloalkyl substituted by at least one unsubstituted heteroaryl, and
—C(O)O—CH$_2$-heteroaryl substituted by a substituent selected from the group consisting of
at least one C$_1$–C$_6$-alkyl,
unsubstituted heteroaryl, and heteroaryl substituted by at least one substituent selected from the group consisting of
C$_1$–C$_6$-alkyl, C$_2$–C$_6$-alkenyl, C$_2$–C$_6$-alkinyl, C$_3$–C$_6$-cycloalkyl and halogen;
R$^2$ is selected from the group consisting of hydrogen and C$_1$–C$_6$-alkyl;
R$^3$ is selected from the group consisting of
unsubstituted aryl,
aryl substituted by at least one substituent selected from the group consisting of
C$_1$–C$_6$-alkyl, C$_2$–C$_6$-alkenyl, C$_2$–C$_6$-alkinyl, C$_3$–C$_6$-cycloalkyl, halogen, cyano,
unsubstituted heteroaryl and
heteroaryl substituted by at least one substituent selected from the group consisting of
C$_1$–C$_6$-alkyl, C$_2$–C$_6$-alkenyl, C$_2$–C$_6$-alkinyl, C$_3$–C$_6$-cycloalkyl, halogen, cyano, and
—C(O)O—(C$_1$–C$_6$)-alkyl;
R$^4$ is selected from the group consisting of hydrogen and C$_1$–C$_6$-alkyl; and
m is 0, 1 or 2;
or a pharmaceutically acceptable salt thereof to a patient in need of such treatment.

* * * * *